United States Patent [19]

Low et al.

[11] Patent Number: 4,851,046

[45] Date of Patent: Jul. 25, 1989

[54] PERIODONTAL OSSEOUS DEFECT REPAIR

[75] Inventors: Samuel B. Low; Alan E. Fetner; Arthur E. Clark, Jr.; Larry L. Hench; June Wilson-Hench, all of Gainesville, Fla.

[73] Assignee: University of Florida, Gainesville, Fla.

[21] Appl. No.: 746,342

[22] Filed: Jun. 19, 1985

[51] Int. Cl.⁴ .............................................. B09K 3/00
[52] U.S. Cl. ....................................... 106/35; 433/217
[58] Field of Search ........................................... 106/35

[56]  References Cited

U.S. PATENT DOCUMENTS 3,981,736  9/1976  Broemer et al. ...................... 501/57
4,239,113 12/1980  Gross et al. .......................... 523/118

Primary Examiner—Theodore Morris
Attorney, Agent, or Firm—Dennis P. Clarke

[57]  ABSTRACT

Method and composition for repair of periodontal osseous defects based on particulate bioactive and biocompatible glass.

9 Claims, 2 Drawing Sheets

SCANNING ELECTRON MICROGRAPH OF
70-910 μm BIOGLASS® PARTICLES

|⎯⎯⎯⎯|
1000 μm

FIG. I.
SCANNING ELECTRON MICROGRAPH OF 70-910 μm BIOGLASS® PARTICLES
⊢—————⊣ 1000 μm

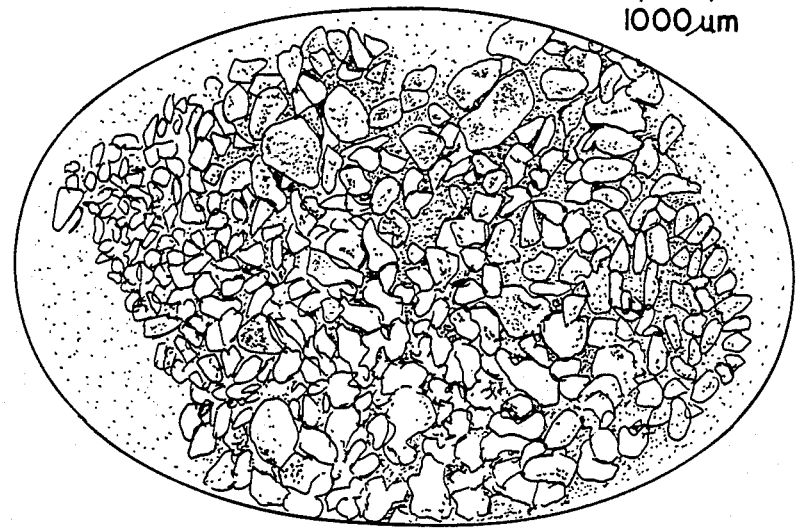

FIG. 2.

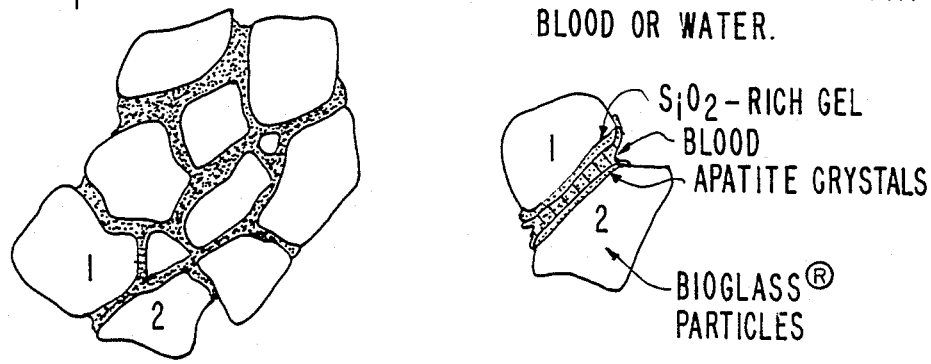

CEMENTING REACTION OF BIOGLASS® IN CONTACT WITH BLOOD OR WATER.

- SiO₂-RICH GEL
- BLOOD
- APATITE CRYSTALS
- BIOGLASS® PARTICLES

COHESIVE MASS OF MIXED PARTICLE SIZE RANGE OF BIOGLASS® POWDERS CEMENTED TOGETHER WITH SILICA-RICH GEL, GROWING APATITE CRYSTALS WITHIN BLOOD FILLING THE SMALL CAPILLARIES BETWEEN THE PARTICLES.

PERIODONTAL OSSEOUS DEFECT REPAIR

BACKGROUND OF THE INVENTION

1. Field of the Invention

The present invention relates to compositions and methods for the repair of periodontal osseous defects.

2. Prior Art

Historically, clinicians have used numerous and varied materials in the attempt to repair periodontal osseous defects. Autogenous grafts have been used with varying degrees of success [Schallhorn, R. G.: Present status of osseous grafting procedures. J. Periodontal 28: 570, 1977; Dragoo, M. R., and Sullivan, H.C.: A clinical and histological evaluation of autogenous iliac bone grafts in humans. Part I, wound healing 2 to 8 months. J Periodontol 44: 599, 1973] but difficulties in obtaining sufficient quantities and the frequent need for a second surgical procedure present obvious disadvantages [Moskow, B. S., Karsh, F., and Stein, S. D.: Histological assessment of autogenous bone--a case report and critical evaluation. J Periodontal 50: 291, 1979.] Allografts [Mellonig, J. T., Bowers, G.M., Bright R. W., and Laurene, J. J.: Clincal evaluation of freeze-dried bone allografts in periodontal osseous defects. J. Periodontal 47: 125, 1976; Sepe, W. W., Bowers, G.M., Lawrence, J. J., Friedlaender, G. E., and Koch, R. W.: Clinical evaluation of freeze-dried bone allografts in periodontal osseous defects. Part II. J Periodontal 49: 9, 1978] have also provided promising results, but limited availability and questions of their immunogenicity still exist [Sanders, J. J., Sepe, W. W., Bowers G. M., Koch, R. W., Williams, J. E., Lekas, J. S., Mellonig, J. T., Pelleu, G. B., Gambill, V.: Clinical evaluation of freeze-dried bone allografts in periodontal osseous defects. Part III. Composite freeze-dried bone allografts with or without autogenous bone grafts. J Periodontal 54: 1, 1983.] In order to overcome these problems, recent attention has been directed toward developing suitable alloplastic materials for such repair procedures.

Tricalcium phosphate ceramic $Ca_3(PO_4)_2$ (TCP) and Hydroxylapatite ceramic $Ca_{10}(PO_4)_6(OH_2)$ (HA) have been widely investigated. These materials are considered biologically inert, producing no inflammatory response when implanted [Jarcho, M., Bolen, C. H., Thomas, M. B., et al.: Hydroxylapatite synthesis and characterization in dense polycrystalline form. J Mater Sci 11: 2027, 1976; Moskow, B. S., Lubarr, A.: Histological assessment of human periodontal defect after durapatite ceramic implant. J Periodontal 54: 455, 1983; Froum, S. Sj., Kushner, L., Scopp, I.W., and Stahl, S.S.: Human clinical and histologic responses to durapatite implants in intraosseous lesions--case reports. J Periodontal 53:719, 1982; Baldock, W. T., Hutchens, Jr., L. H., McFall, Jr., W. T., Simpson, D. M.: An evaluation of tricalcium phosphate implants in human periodontal osseous defects of two patients, J. Periodontal 56:1, 1985] Rabalais, M. L., Yukna, R.A., and Mayer, E.T. [Evaluation of durapatite ceramic as an alloplatic implant in periodontal osseous defects. I. Initial six month results. J. Periodontal 52: 680, 1981] found, on reentry, greater fill with HA (durapatite) than debridement alone. Others [Nery, E. B., and Lynch, K. L.: Preliminary studies of bioceramic in periodontal osseous defects. J. Periodontal 49: 523, 1978; Strub, J. R., Gaberthuel, T.W. and Firestone, A.R.: Comparison of tricalcium phosphate and frozen allogenic bone implants in man. J Periodontal 50: 624, 1979] have found similar bone fill with TCP. However, histologic evaluations have given little evidence of new attachment with either of these materials [Moskow, B. S., Lubarr, A.: Histological assessment of human periodontal defect after durapatite ceramic implant. J Periodontal 54: 455, 1983; Froum, S. Sj., Kishner, L., Scopp, I. W., and Stahl, S. S.: Human clinical and histologic responses to durapatite implants in intraosseous lesions--case reports. J Periodontal 53: 719, 1982; Meffert, R.M., Thomas, J. R., Hamilton, K. M., Brownstein, C. N.: Hydroxylapatite as an alloplastic graft in the treatment of human periodontal osseous defects. J Peridontal 56: 63–74, 1985.]

Bioactive and biocompatible glasses have been developed as bone replacement materials. Studies have shown that these glasses will induce osteogenesis [Hench, L. L., Splinter, R. J., Allen, W.c. et al: Bonding mechanisms at the interface of ceramic prosthetic materials. J Biomed Mater Res 1971; 5: 117–141; Hench, L. L., Paschall, H.A.: Direct chemical bond of bioactive glass-ceramic materials to bone and muscle. J Biomed Mater Res 1973; 7:25–42; Clark, A.E. ©Pantano ©C.G. ©and Hench, L. L.: Compositional Analysis of the formation of a bone-implant bond, Symposium on materials for reconstructive surgery, Clemson University, April, 1975; Clark, A. E., Paschall, H. A., and Hence, L. L.: The influence of surface chemistry on implant interface histology; A theorectical basis for implant materials selection, J Biomed Materials Research, Vol. 10, No. 2, pg. 161–174, March, 1976; Hench, L.L., and Wilson, J.: Surface-Active biomaterials. Science 226, pp. 630–636, 1984; Hench, L. L., and Clarke, A.E.: "Adhesion of bone", Biocompatibility of Orthopaedic Implants, Vol. II, Editor-David F. Williams, pg. 129–170, CRC Press, Inc., Boca Raton, Florida, 1982] when implanted in bone. The interfacial bond between the implant and bone has been demonstrated to be extremely strong [Piotrowski, G., Hence, L. L., Allen, W. C., and Miller G. J.: Mechanical Studies of the Bone Bioglass Interfacial Band. J. Biomed Mater Res. Symp, 9: 47–61, 1975.]

The so-called 4555 or S, bioactive glass formulation has been widely tested. The substitution of $CaF_2$ (calcium fluoride) for a variable percentage of the CaO (calcium oxide) yields the F formulations. Toxicology evaluation of the glasses [summarized by Wilson, J., Schoen, R. J., Pigott, G. H., et al: Toxicology and biocompatibility of bioglasses. J Biomed Mater Res 1981; 805–817] has shown no toxic effects in bone or soft tissue in numerous in vitro and in vivo models.

The bonding of the glass to bone begins with exposure of the glass to aqueous solutions. Na+ in the glass exchanges with H+ from the body fluids causing the pH to increase. Ca and P migrate from the glass forming a Ca-P rich surface layer. The thickness of the Ca-P rich zone remains at 30–40 microns with an underlying silica rich zone slowly increasing in dimension as the Na+ in the glass continues to exchange with the H+ of the solution.

Initially the Ca-P rich layer is amorphous, but within 7–10 days it crystalizes into an hydroxyapitite-like material. Collagen, either in vitro or in vivo, becomes structurally integrated in the apatite aggomerates. A zone forms between the collagen and surface active glass in vivo that is 80–100 nm thick. Osteoblasts in the implant area provide (1) collagen and ground substance, and (2) matrix vesicles for primary mineralization [Gross, U.

M., Strunz, V.: Clin. App. Biomaterials, EDS. Albrektsson and Branemark, J. Wiley, pp. 237, 1982.] As maturation continues, evenly distributed osteocytes can be observed.

The behavior of the bioactive glasses as solid implants in a dental application was examined by Stanley, H., Hench, L. L., Going, R., Bennett, C., Chellemi, S. J., King, C., Ingersoll, N., Etherridge, E., and Kreutziger, K. ["The implantation of natural tooth from bioglasses in baboons," Oral Surg. Oral Med. Oral Path., 42, (3), 339-356, 1976.] Replicate tooth forms of glass were fabricated and implanted into extracted incisor sockets of adult baboons. Distinct histopathologic features were associated with the specific formulation used. After six months, the F glass formulation induced ankylosis while another glass formulation induced a fibrous capsule. In the two successful S implants, ankylosis was induced in one with the other producing an apparently normal periodontal ligament. A two year study [Stanley, H. R., Hench, L. L. Bennett, Jr., C. G. Chellemi, S. J. King, C.J. Going, R. E., Ingersoll, N. L., Ethridge, E. C., Kreutziger, K. L., Loeb, L., Clark, A. E.: "The implantation of Natural Tooth From Bioglass in Baboons-Long Term Results," The International Jour of Oral Implantology, pg. 26-36, Vol. 2:2, 1981] consistently found ankylosis of both the F and S formulations.

It is an object of the present invention to provide bioactive and biocompatible glass compositions specifically suitable for the repair of periodontal osseous defects.

SUMMARY OF THE INVENTION

The present invention provides a composition suitable for the repair of periodontal osseous defects comprising particulate bioactive and biocompatible glass optionally and preferably adversed with a liquid in an amount sufficient to wet the particles of glass, the particulate glass having a particle size in the range of from about 90 to about 710 $\mu$m and the following weight percentage composition:

| Component | Weight Percentage |
| --- | --- |
| $SiO_2$ | 40-52 |
| CaO | 10-50 |
| $Na_2O$ | 10-35 |
| $P_2O_5$ | 2-8 |
| $CaF_2$ | 0-25 |
| $B_2O_3$ | 0-10 |

The invention also provides a method of repairing a periodontal osseous defect comprising applying the above composition to the defect and allowing the composition to harden and bond to surrounding tissue.

DETAILED DESCRIPTION OF THE INVENTION

Figure 3:
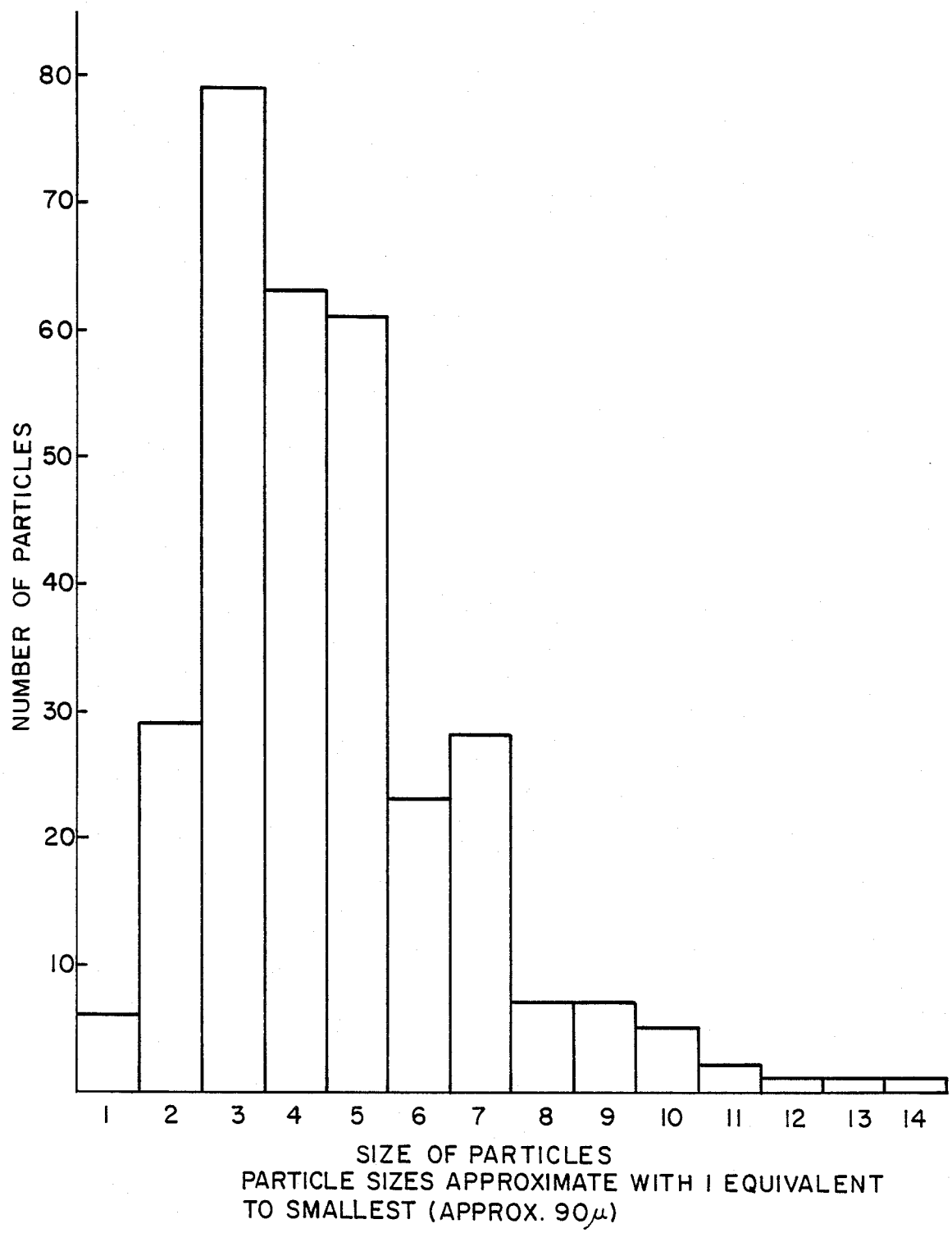

Presently available synthetic materials for use in the repair of periodontal defects have particle sizes in the range of 250 to 500 $\mu$m (Zaner and Yukna J. Periodontal, Vol. 55(7) Page 406 (1984). Autogeneous bone samples have a size ranging from $210 \times 105$ $\mu$m for autogeneous bone blend to $1559 \times 783$ $\mu$m for autogeneous hand chisel bone samples.

In-vitro experiments consisting of the mixing of equal volumes of human blood with equal volumes of presently used synthetic materials showed that the mixtures were not cohesive. The tricalcium phosphate (TCP) material (Synthograft) was especially noncohesive and tended to float on top of the blood when the mixing action stopped. This is due to the microporous nature of the particles of Synthograft.

Manipulation of the hydroxyapatite (HA) and tricalcium phosphate (Synthograft) powders with a flat instrument such as a spatula or orban knife was exceedingly difficult even after mixing with blood. Manipulation of the HA and TCP powders mixed with sterile physiological saline was not improved. In each of these instances it was discovered that only a few granules of the powders remained on the instrument as they were moved from the mixing dish to a simulated periodontal defect. Efforts to pack the HA and TCP powders, either dry or mixed with blood or saline into a simulated periodontal defect did not result in a cohesive, space-filling mass. Instead the particles cound be easily removed by suction or slight irrigation. See Table 1.

In contrast to the above observations of the noncohesiveness of presently used synthetic periodontal grafting materials, it was an unexpected discovery that bioactive glass powders of the above compositions and of a specific range of sizes, specific surface areas, specific pore distributions, and specific surface chemistry would form a cohesive mass when mixed with blood.

When quantities of blood, ranging from equal volume to one-third equal volume to glass powders, but of sufficient volume to wet thoroughly the glass powder, were mixed for a few seconds to one-half minute with 45S5 and 45S5F glass powders it was discovered that the particles stuck together and quickly formed a putty-like consistency. The resulting cohesive mixture could be easily picked up by an instrument, both flat and pointed, and passed from the mixing vessel to a simulated implantation site very easily. The cohesive mass of glass powder and blood stuck to the instrument with sufficient cohesion that the mass could be pressed into a simulated site without loss of particles. The resulting cohesive mass once placed in the site remained in place after suction or irrigation.

It was further noted that specific size ranges of glass powders were substantially more cohesive than others. The glass powder comprised of 90-355 um particles easily formed a cohesive mass and was easily manipulated. The larger powder comprised of 500-710 $\mu$m particles was less effective in forming a cohesive mass and being manipulated. This behavior was attributed to the smaller surface area of the 500-710 $\mu$m powder. However, even the 500-710 $\mu$m glass powder was still markedly superior in cohesion and manipulation to HA or TCP powders. Addition of 90-355 $\mu$m glass particles to the previously mixed 500-710 $\mu$m glass powder-blood mixture improved both cohesiveness and workability. This suggested that a larger particle size range might produce a more clinically desirable mixture. To test this hypothesis a mixture of equal weight by thirds of 90-355 $\mu$m glass particles, 355-500 $\mu$m glass particles, and 500-710 $\mu$m glass particles (total size range 90-710 $\mu$m) was mixed with blood. The resulting mixture formed an even more cohesive and dense mass with the most superior performance in handling and manipulation.

TABLE 1
Behavior of Synthetic Periodontal Packing Materials

| Materials | Particle Size (μm) | Ease of Manipulation | Cohesiveness with blood | Appearance in Periodontal Defect |
|---|---|---|---|---|
| Synthograft (tricalcium phosphate) | 250–500 | very poor, fell off instrument | none | washed away from site with bleeding |
| Augmen (porous tri-calcium phosphate) | 700–1000 | very poor, fell off instrument | none | washed away from site with bleeding |
| periograf (hydroxylapatite) | 280–500 | poor, tendency to fall off instrument | none | tended to wash from site with bleeding |
| alreograf (hydroxyapatite) | 700–1000 | poor, tendency to fall off instrument | none | tended to wash from site with bleeding |
| Glass 45S5 or 45S5F | 500–710 | good remained on instrument | good | moderately, densely packing of particles filling defect |
| Glass 45S5 or 45S5F | 90–355 | very good easy to handle & transport | very good, easily packed | very good, dense packing, resistant to irrigation |
| Glass 45S5 or 45S5F | 90–710 | excellent superb adhesion to instrument, superb ease of transport | excellent superior packing | very dense packing in site, translucent, appears in site as if bone resistant to irrigation and suction |

The invention is illustrated by the following non-limiting example.

EXAMPLE

Six adult Patas monkey (*Erythrocebus patas*) (five females and one male) were used in the study. The Patas monkey is similar in size and dentition to the Rhesus monkey (*Macaca mulatta*). All animals had moderate gingivitis associated with heavy supragingival plaque and calculus accumulations. Using Ketamine Hydrochloride (100 mg/ml; 10 mg/kg body weight) the animals received a twice weekly oral hygiene regiment consisting of toothbrushing and 2% chlorhexidine gluconate rinses. The regiment was similar to the one established by Caton, J.G.: Establishing and maintaining clinically healthy gingivae in rhesus monkeys. J. Clin Periodontal 6: 260, 1979. The first two cleanings required mechanical instrumentation with ultrasonics and hand instrumentation for removal of calcified deposits. The reduction in clinical inflammation was sustained by continuation of the regiment throughout the study.

Bioactive glasses (Table 2) were prepared by placing the premixed components into a covered platinum crucible, melting at 1350° C. and pouring the contents into a container of water. The resultant glass frit was washed with acetone, ground with a mortar and pestle and sized with a series of calibrated sieves. Three different particle size ranges were obtained for each of the two formulations (Table 3).

TABLE 2

| | Implant Composition (Weight Percent) | | | | |
|---|---|---|---|---|---|
| | $SiO_2$ | CaO | $CaF_2$ | $Na_2O$ | $P_2O_5$ |
| S (45S5) | 45 | 24.5 | | 24.5 | 6 |
| F (45S5.4F) | 43 | 14 | 13 | 24 | 6 |

TABLE 3

| | Particle Size |
|---|---|
| | Size (Microns) |
| S Bioglass | 90–355 |
| S Bioglass | 500–710 |
| S Bioglass | 90–710 |
| F Bioglass | 90–355 |
| F Bioglass | 500–710 |
| F Bioglass | 90–710 |

After a minimum of five weeks of the oral hygiene phase, the monkeys were taken to surgery. Inhalation general anesthesia via nasal intubation was administered. Local anesthesia (2% Lidocaine with epinephrine 1:100,000) was infiltrated. Full thickness mucoperiosteal flaps were elevated and the area was debrided. The teeth were notched at the level of the boney crest with a #¼ round carbide bur in a slow speed handpiece. Osseous defects four to five millimeters deep were created with a high speed handpiece using a #2 or a #4 round carbide bur and copious water irrigation. Root planing was accomplished with flame-shaped diamonds and finishing burs followed by hand instrumentation. Most sites prepared were two-walled interproximal defects, but tooth proximity and other anatomical considerations required the creation of three wall lingual or palatal defects adjacent to some teeth. On lower speed premolars (two-rooted teeth), lingual sites were prepared with removal of furcation bone simulating a deep class II furcation involvement.

Each animal had a total of eighteen sites available for implantation. Twelve sites received a bioactive glass implant. Four sites were implanted with Synthograft, (Johnson & Johnson Dental Products, East Windsor, New Jersey,) Augmen, (Miter Inc., Columbus, Ohio,) Periograf and Alverograf (Cook-Waite Laboratories, Inc., New York, N.Y.) Two sites per animal served as controls.

The materials were mixed with physiological saline in a disposable dish and packed into the defect. Flaps were replaced with 4:0 chromic sutures and the animals were placed on a softened diet for two weeks.

Starting the day of the surgery and for six days thereafter the animals were given daily (IM) injections of Achromycin [Lee Sepe, W.W., Bowers, G.M., Laurence, J.J., Friedlaender, G.E., and Koch, R.W.: Clinical evaluation of freeze-dried bone allografts in periodontal osseous defects. Part II. J.Peroidontal 49:9, 1979] (Tetracycline Hcl) (20 mg/kg.]

The animals were sacrificed by overdose of sodium pentobarbital on the following time schedule: one animal at one month, two animals at four months and three animals at six months. The jaws were removed and placed in 10% formalin. After fixation, they were decalcified and subdivided into small blocks each containing an experimental site. The tissues were embedded in paraffin, sectioned at approximately 6 microns and stained with hematoxylin and eosin.

When the various powders were implanted in the monkey model during the study the procedure was essentially the same as described above in the in-vitro experiment. Prior to placement, the materials were wet with one or two drops of sterile physiological saline to essentially wet an area that was to be used. The materials were carried from the dish with an orban knife or equivalent flat type instrument and carried to the periodontal site which was prepared to be approximately 4-5 mm deep. Most of these sites were bleeding because they were surgically created sites.

The glass powders were easily transported to the site, and had the ability to pack very densely into the defects. On clinical evaluation it was found that the material seemed to have a hemostatic property in that is was able to completely fill the defect and appeared to stop the bleeding. The glass powders mixed well with blood and formed a cohesive mix, which stopped the bleeding either due to intrinsic hemostatic properties or due to an efficient filling of the defect such that it provided a physical barrier to bleeding.

The densely packed glass powders within the periodontal defects appeared translucent and with sufficient packing density that it appeared as if the bone had never been removed.

It was found that this quality existed for all three of the particle size ranges of glass powders regardless of whether it was the S or the F fluoride forumulation. The 500 to 710 $\mu$m powders were the least effective of the three. The 90 to 710 $\mu$m powders were the most effective particle size range. The 90 to 355 $\mu$m powders were in between the two in manipulation and packing properties. These clinical results in Patus monkeys were equivalent to the in-vitro findings described above. The glass powders were compared in the in vivo monkey model, with tricalcium phosphate (Synthograf) which had a small particle size range of 250 to 500 $\mu$m, and Augmen, which is a porous tricalcium phosphate, (TCP) in the 700 to 1000 $\mu$m particle size range. When implanting these materials into sites, there are difficulty in manipulating the material. When they are wet in the same way as glass, with sterile physiological saline, the materials were not cohesive, and were difficult to carry to the sites. They fell off of the instruments and were lost. When placed in a site that was bleeding, the TCP materials seemed to float or not stay in the defect and, with bleeding, washed out. There was a great difference between these TCP materials and glass material in that the glass was hemostatic and it seemed that tricalcium phosphate caused increased bleeding.

The hydroxylapatite (HA) powders tested were Periograf which is equivalent in size (250-500 $\mu$m to Synthagraf (TCP). Alveograf (HA) and Augment (TCP) are ridge augmentation materials of a larger particle size (700 to 1000 $\mu$m). These HA materials handled slightly better, Table 1, than tricalcium phosphates although they still could not be manipulated properly. They tended to fall off of the instrument and when placed in a bleeding surgically created defect tended to float out. Their packability in the periodontal defect was markedly inferior to glass powders of all size ranges. These materials had even poorer manipulation properties when implanted in a living model than in the in-vitro test.

Another superior property noted for glass composition was that when implanted into a site they was translucent and not visibly different from normal tissue. When suction was placed adjacent to the glass after implantation, it remained inside the defect and was resistant to surgical suction. This was not the case with either the TCP or HA calcium phosphate powders; suction could remove all these implant material from the defect very quickly. In contrast, materials made from hydroxylapatite are visible as opaque white areas beneath the gingeva. Histological examination of the periodontal defects after one month showed that with the optimum (90-710 $\mu$m) range of particle sizes of glass powders the following:

1. The material was retained in the implant area.
2. Adhesion of collagen to the large particles with no inflammation.
3. The dento gingeval collagen fibers of the gingeval which by insertion into the cementum of the tooth, prevent epthelial migration downward, are continuous with the collagen adherent to the larger glass particles.
4. The larger glass particles at the base of the implant site in contact with repairing bone become bonded to and surrounded by the new bone.
5. Superficial gingivitis does not extend into the implanted area filed with 90-710 $\mu$m glass particles.
6. There is minimal epithelelial migration into the implanted area.
7. The smallest glass particles were removed by macrophages and giant cells leaving space gradually infiltrated by adherent collagen and/or bone.

The consequences of the above 7 observations is that the periodontal defect becomes filled by large particles of glass with adherent collagen fibers and newly formed bone. Another consequence is that the transseptal fibers are continuous between neighboring teeth and large glass particles thereby minimizing epithelial downgrowth in the defect.

Thus, the compositions of the invention are partially biodegradable in that smaller size particles are replaced ultimately by an ingrowth of tissue which serves to further lock the implant in place. The larger particles function to form a bond with the surrounding tissue.

These above cited seven observations and the overall beneficial histological and physiological consequences of using the 90-710 $\mu$m glass powders in a periodontal defect are an unexpected contrast to the behavior of TCP powders presently in use. The TCP powders provoke a strong inflammatory and giant cell reaction regardless of particle size, i.e., even the large 500-700 $\mu$m TCP particles are being actively removed from the defect without restoration of the transseptal fibers and without prevention of epithelial migration. These observations of the presently used TCP materials are indicative of an unsatisfactory repair of the periodontal defect which are consistent with long term clinical findings for the TCP materials, even though they are sill on the market.

In order to understand the unexpected differences in in-vitro and in-vivo behavior of glass powders compared with HA and TCP powders, physical characterization studies were undertaken. These studies showed that there are unexpected substantial physical differences between the synthetic hydroxyapatite and tricalcium phosphate materials as compared with the glass powders.

Table 4 is a compilation of results from nitrogen absorption isotherm analysis of the various powders tested in the in-vitro and the in-vivo experiments. The BET surface areas are listed in the first column, the total pore volume is in the second and the average pore radius calculated from the nitrogen absorption isotherm is in the 3rd column. It is apparent from this data that the synthetic apatite (HA) and tricalcium phosphate (TCP) materials have substantially more surface area per unit weight of material than the glass powders,. The total pore volume varies for the materials in such a way that it does not show a consistent difference. However, the average pore radius of the HA and TCP materials is substantially less than the average pore radius of the glass materials.

The very small average pore radius for the synthetic HA and TCP materials is due to microporosity of the materials which gives rise to their low density and tendency to float from the site when impacted into the periodontal defect. In contrast, the average pore radius of the glass powders is largely controlled by the geometric packing of the particles into a cohesive mass. The glass powders do not show the very small microporosity characteristic of the presently used materials and therefore there is no tendency for them to float in the presence of the blood of the periodontal defect.

TABLE 4

| SAMPLE | BONE GRAFTING MATERIAL | | |
|---|---|---|---|
| | (BET) SA | TOTAL PORE VOLUME | AVERAGE PORE RADIUS |
| Alveograf | 1.49 m$^2$/g | 5.33 × 10$^{-3}$ cc/g | 71.2 Å |
| Augmen | 1.16 m$^2$/g | 3.84 × 10$^{-3}$ cc/g | 65.9 Å |
| Periograf | 1.10 m$^2$/g | 2.22 × 10$^{-3}$ cc/g | 40.3 Å |
| Synthograft | 1.90 m$^2$/g | 4.92 × 10$^{-3}$ cc/g | 51.8 Å |
| 90-710 μm 45S5F | 0.52 m$^2$/g | 8.35 × 10$^{-3}$ cc/g | 319 Å |
| 90-710 μm 45S5F | 0.054 m$^2$/g | 6.89 × 10$^{-4}$ cc/g | 254 Å |
| 500-710 μm 45S5F | 0.024 m$^2$/g | 5.23 × 10$^{-4}$ | 431 Å |
| 90 355 μm 45S5F | 0.101 m$^2$/g | 7.84 × 10$^{-4}$ cc/g | 155 Å |
| 500-710 μm 45S5F | 0.092 m$^2$/g | 7.14 × 10$^{-3}$ cc/g | 1546 Å |
| 90-355 μm 45S5F | 0.941 m$^2$/g | 1.16 × 10$^{-2}$ | 247 Å |

Note: All samples outgassed 20 hrs. @ 250° except (Alveograf = 44 hrs.) and (90-355, 45S5F = 96 hrs.)

The geometric packing of the glass powders of the wide particle size range results in a morticing of the small particles within the interstices of the large particles. Even a dry arrangement of this broad size range of glass powders, such as shown in a scanning electron micrograph (FIG. 1) illustrates how the particles can fit together into a tightly packed array. FIG. 3 shows the size distribution as measured in the micrograph of FIG. 1.

The instantaneous chemical reaction of the glass particles with water and/or blood gives rise to the formation of a surface silica rich gel layer within which hydroxyapatite microcyrstallites can form. When the gel formation and apatite crystallites occur within the capillary space separating the particles a cohesive mass results. (FIG. 2) The cohesive mass remains attached together during the insertion of it into the periodontal defect and the tight mechanical packing is responsible for the stoppage of bleeding. This hemostatic effect observed for the glass periodontal pack is due to the mechanical impedance or occlusion of the bleeding capillary bed.

Results showing that it is mechanical occlusion of the blood supply in the periodontal defect rather than an alteration of blood chemistry were obtained during measurements on whole blood clotting time for the variety of implant materials tested in the in-vitro and in-vivo experiments. Table 5 compares the results from this clotting experiment. It can be seen from this table that there is not significant difference between the control clotting time of 4.34 minutes and the glass S formulas of 90 to 710 μm particle size and 500 to 710 particle size. Each of those sizes results in 4.3 minutes of clotting time. The F formula glass powders do decrease clotting time to values that are akin to the synthetic Periograft and Synthograft and Augmen materials. However, the HA and TCP materials are not hemostatic in the periodontal defect whereas both the glass S formula and glass F formulas are. Consequently it can be concluded from these results that the interfacial surface chemistry of the glass is not responsible for the superb clotting behavior in the periodontal defect. Instead it must be mechanical occlusion due to tight cohesiveness of the glass particles in their optimum size and their rapid interfacial surface reactions that form a cementing of particles by the gel and apatite interfacial phases as soon as they are in contact with water and/or blood.

TABLE 5

WHOLE BLOOD CLOTTING TIME
(Test used 2 ml whole blood and 0.35 ml of test material)

| | (time/minutes) |
|---|---|
| Control (0.35 ml saline) | 4.34 |
| Periograf | 3.30 |
| Synthograft | 4.00 |
| Bioglass S (500-710 μm) | 4.30 |
| Bioglass S (90-710 μm) | 4.30 |
| Bioglass F (90-355 μm) | 3.30 |
| Bioglass F (500-710 μm) | 4.00 |
| Bioglass F (90-710 μm) | 3.40 |

TABLE 5-continued

WHOLE BLOOD CLOTTING TIME
(Test used 2 ml whole blood and 0.35 ml of test material)

| | (time/minutes) |
|---|---|
| Augmen | 3.00 |

Bioactive and biocompatible glasses of the following weight percentage compositions may also be employed in the practice of the invention:

| (1) | Component | Weight Percentage |
|---|---|---|
| | $SiO_2$ | 45 |
| | CaO | 24.5 |
| | $Na_2O$ | 24.5 |
| | $P_2O_5$ | 6.0 |

| (2) | Component | Weight Percentage |
|---|---|---|
| | $SiO_2$ | 45 |
| | CaO | 12.25 |
| | $Na_2O$ | 24.5 |
| | $CaF_2$ | 12.25 |
| | $P_2O_5$ | 6.0 |

| (3) | Component | Weight Percentage |
|---|---|---|
| | $SiO_2$ | 40 |
| | CaO | 24.5 |
| | $Na_2O$ | 24.5 |
| | $P_2O_5$ | 6.0 |
| | $B_2O_3$ | 5.0 |

| (4) | Component | Weight Percentage |
|---|---|---|
| | $SiO_2$ | 52 |
| | CaO | 21.0 |
| | $Na_2O$ | 21.0 |
| | $P_2O_5$ | 6.0 |

We claim:

1. A composition adapted for the repair of periodontal osseous defects consisting essentially of particulate bioactive and biocompatible glass, said particulate glass having a particle size in the range of from about 355 to about 710 μm and the following weight percentage composition:

| Composition | Weight Percentage |
|---|---|
| $SiO_2$ | 40-52 |
| CaO | 10-50 |
| $Na_2O$ | 10-35 |
| $P_2O_5$ | 2-8 |
| $CaF_2$ | 0-25 |
| $B_2O_3$ | 0-10 |

2. The composition of claim 1 wherein said particulate glass has a particle size in the range of from about 355 to about 500 μm.

3. The composition of claim 1 wherein said particulate glass has a particle size in the range of from about 500 to about 710 μm.

4. The composition of claim 1 consisting essentially of a mixture of (1) said particulate glass having a particle size in the range of from about 90 to about 350 μm, (2) said particulate glass having a particle size in the range of from about 355 to 500 μm, and (3) said particulate glass having a particle size in the range of from about 500 to 710 μm.

5. The composition of claim 4 consisting essentially of equal weights by thirds of each of said particulate glasses (1), (2) and (3).

6. The composition of claim 1 additionally containing a liquid in admixture with said particulate glass in an amount sufficient to wet the particles of said glass.

7. The composition of claim 6 wherein said liquid is aqueous.

8. The method of claim 6 wherein said liquid is blood.

9. The composition of claim 7 or claim 8 wherein the amount of said aqueous liquid or blood in said mixture is from about ⅓ to about equal volume of said particulate glass.

* * * * *

UNITED STATES PATENT AND TRADEMARK OFFICE
CERTIFICATE OF CORRECTION

PATENT NO. : 4,851,046

DATED : July 25, 1989

INVENTOR(S) : Samuel B. Low et al.

It is certified that error appears in the above-identified patent and that said Letters Patent is hereby corrected as shown below:

Column 12, line 34 (claim 8) for "method" read --composition--

Signed and Sealed this

Twenty-ninth Day of April, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 4,851,046
DATED : July 25, 1989
INVENTOR(S) : Samuel B. Low et al.

It is certified that error appears in the above-indentified patent and that said Letters Patent is hereby corrected as shown below: Title page,
Under the heading "[75] Inventors:", additionally read --Caleb J. King, Gainesville, Florida--.

Signed and Sealed this

Sixteenth Day of December, 1997

Attest:

BRUCE LEHMAN

Attesting Officer            Commissioner of Patents and Trademarks